United States Patent [19]

Liu

[11] Patent Number: 5,456,696
[45] Date of Patent: * Oct. 10, 1995

[54] MONOFILAMENT SUTURE AND PROCESS FOR ITS MANUFACTURE

[75] Inventor: Cheng-Kung Liu, Norwalk, Conn.

[73] Assignee: United States Surgical Corporation, Norwalk, Conn.

[ * ] Notice: The portion of the term of this patent subsequent to Jun. 8, 2010 has been disclaimed.

[21] Appl. No.: 94,816

[22] Filed: Jul. 20, 1993

[51] Int. Cl.⁶ ................................................. A61B 17/04
[52] U.S. Cl. .......................................... 606/228; 606/231
[58] Field of Search ..................... 606/228–231; 264/210.8, 289.6, 290.5, 235.6; 428/375, 421

[56] References Cited

U.S. PATENT DOCUMENTS

| | | |
|---|---|---|
| 2,212,772 | 8/1940 | Graves . |
| 2,226,529 | 12/1940 | Austin . |
| 3,124,632 | 3/1964 | Larkin et al. . |
| 3,156,750 | 11/1964 | Cuculo . |
| 3,359,983 | 12/1967 | Northey et al. . |
| 3,436,450 | 4/1969 | Specker et al. . |
| 3,630,205 | 12/1971 | Listner . |
| 3,739,055 | 6/1973 | Ueda et al. . |
| 3,792,010 | 2/1974 | Wasserman et al. . |
| 4,338,277 | 7/1982 | Saito et al. . |
| 4,470,941 | 9/1984 | Kurtz . |
| 4,520,822 | 6/1985 | Menezes et al. . |
| 4,550,730 | 11/1985 | Shalaby et al. . |
| 4,557,264 | 12/1985 | Hinsch . |
| 4,620,542 | 11/1986 | Menezes et al. . |
| 4,621,638 | 11/1986 | Silvestrini . |
| 4,911,165 | 3/1990 | Lennard et al. . |
| 5,007,922 | 4/1991 | Chen et al. . |
| 5,217,485 | 6/1993 | Liu et al. . |
| 5,236,444 | 8/1993 | Muth et al. . |
| 5,269,807 | 12/1993 | Liu . |

FOREIGN PATENT DOCUMENTS

| | | |
|---|---|---|
| 0423807 | 4/1991 | European Pat. Off. . |
| 0415783 | 6/1991 | European Pat. Off. . |
| 53-24417 | 3/1978 | Japan . |
| 54-27023 | 3/1979 | Japan . |
| 57-139513 | 8/1982 | Japan . |
| 59-157314 | 9/1984 | Japan . |
| 1588031 | 4/1981 | United Kingdom . |

Primary Examiner—Gary Jackson

[57] ABSTRACT

A process and apparatus are provided for preparing monofilament sutures of improved physical characteristics.

7 Claims, 1 Drawing Sheet

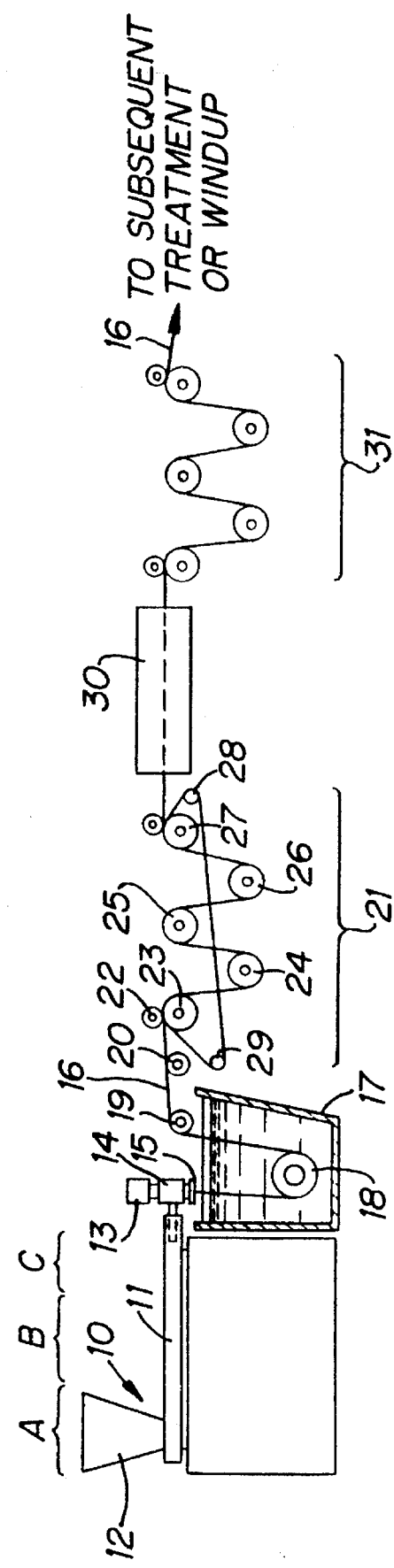

MONOFILAMENT SUTURE AND PROCESS FOR ITS MANUFACTURE

BACKGROUND OF THE INVENTION

This invention relates to a monofilament suture exhibiting improved physical properties such as straight-pull strength, knot-pull strength and elongation and to a process for its manufacture.

Methods for making monofilaments that are suitable for use as surgical sutures are known and generally include the steps of extruding at least one bioabsorbable or nonbioabsorbable polymer to provide a monofilament, quenching the monofilament to effect its solidification, drawing, or stretching the solidified monofilament to achieve molecular orientation and annealing the drawn monofilament to relieve internal stresses. See, e.g., U.S. Pat. Nos. 3,092,891, 3,106,442, 3,630,205, 4,911,165, 5,217,485 and U.K. Patent Specification No. 1,588,031 and European Patent Application No. 415,783.

SUMMARY OF THE INVENTION

It has been discovered that if in a monofilament suture manufacturing process the solidified monofilament is allowed to dwell at ambient conditions for a predetermined period of time prior to being drawn the resulting suture will exhibit increased strength, i.e., tenacity, and improved physical properties such as straight-pull strength, knot-pull strength and elongation.

In accordance with this invention, in a continuous monofilament suture manufacturing process in which a thermoplastic polymer is melt extruded and quenched to provide a solidified monofilament and the solidified monofilament is subjected to drawing and annealing to provide the suture, an improvement is provided which comprises delaying the stretching operation in order to expose the solidified monofilament to ambient conditions for a predetermined extended period of time ranging from about 2 to about 30 minutes. The step of exposing the solidified monofilament to ambient conditions prior to drawing is hereinafter referred to as the "aging" step. The monofilament which is thus aged prior to drawing may then be drawn and annealed in a manner known in the art to provide a monofilament suture exhibiting improved properties.

BRIEF DESCRIPTION OF THE DRAWINGS

FIG. 1 is a schematic illustration of an apparatus which is suitable for carrying out the extruding, quenching, aging and stretching steps of the monofilament suture manufacturing process of this invention.

DESCRIPTION OF THE PREFERRED EMBODIMENTS

In general, the conditions of the individual steps of extruding, drawing and annealing in the monofilament suture manufacturing process of this invention can be substantially the same as those disclosed in U.S. Pat. No. 5,217,485, the contents of which are hereby incorporated by reference herein. Similarly, the process herein can employ much the same type apparatus as that described in U.S. Pat. No. 5,217,485.

FIG. 1 schematically illustrates a particularly useful manufacturing operation for the extrusion, quenching, aging and stretching operations of a monofilament. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polymer are introduced to the extruder through drier-hopper 12. Suitable polymers include those that are bioabsorbable and nonbioabsorbable. Examples of bioabsorbable polymers which can be employed in the process of this invention include polymers, copolymers and polymeric blends derived from monomers known to provide biocompatible, bioabsorbable polymers. Such monomers include glycolide, glycolic acid, lactide, lactic acid, p-dioxanone, trimethylene carbonate, epsilon-caprolactone, dimethyltrimethylene carbonate, 1,5dioxepen-2-one and the like. Polymers derived in whole or in part from p-dioxanone, particularly homopolymers of p-dioxanone, are preferred in the practice of this invention. Methods of making polymers of p-dioxanone are known. See, for example, U.S. Pat. No. 4,052,988 to Doddi et al. the disclosure of which is incorporated herein by reference. Examples of nonbioabsorbable polymers which can be employed in the process of this invention include polyethylene, polypropylene, nylon, polyethylene terephthalate, and the like.

Motor-driven metering pump 13 delivers melt extruded polymer at a constant rate to spin pack 14 and thereafter through a spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm. If desired, a chimney (not shown), or shield, can be provided to reduce the length of the air gap, e.g. from 1 to 10 cm, thereby isolating monofilament 16 from contact with air currents which might otherwise affect the cooling of the monofilament in an unpredictable manner. Monofilament 16 is passed through quench bath 17 around driven roller 18 and over idle rollers 19 and 20. Optionally, a wiper (not shown) may remove excess water from the monofilament as it is removed from quench bath 17. On exiting the quench bath the monofilament enters first godet station generally indicated at 21.

First godet station 21 is equipped with five individual godets around which monofilament 16 is wrapped. First godet 23 is provided with nip roll 22 to prevent slippage which might otherwise result. Upon entering first godet station 21, monofilament 16 passes over first godet 23, under second godet 24, over third godet 25, under fourth godet 26 and over fifth godet 27. Fifth godet 27 is proximally located to separation roller 28 which is provided with a plurality of laterally spaced circumferential grooves which act as guides for monofilament 16. After monofilament 16 passes over fifth godet 27 it wraps around a groove on separation roller 28 and extends back to and around a corresponding groove on separation roller 29 located proximal to first godet 23. Monofilament 16 wraps around separation roller 29, ascends up to first godet 23 and continues onward to the remaining godets in the manner just described. When the monofilament passes over the fifth godet 27 a second time, it may be wrapped around a second groove on separation roller 28. The monofilament then extends back to separation roller 29 and around a corresponding groove thereon. The monofilament may pass through first godet station 21 any desired number of times. The solidified monofilament is thus allowed to dwell at ambient conditions before the monofilament enters heating unit 30. In this fashion monofilament 16 is aged or exposed to ambient conditions for a desired period of time prior to being stretched. The solidified monofilament can be exposed to ambient conditions for a predetermined extended period of time of at least two minutes. In one embodiment the solidified monofilament can be exposed to ambient conditions for a period ranging from about 2 to about 30 minutes.

It is to be understood that aging or exposing the monofilament to ambient conditions for a predetermined period of time prior to drawing the monofilament can be accomplished in many different ways. For example, any number of godets may be employed to provide the dwell period. In addition, the arrangement of the godets can be varied. Also, other structure suitable for providing aging of the monofilament prior to stretching will be apparent to those skilled in the art.

Monofilament 16 passing from godet station 21 is stretched to effect its orientation and thereby further increase its tensile strength. Stretching may be achieved by cold drawing the monofilament or drawing the monofilament while or after it has been heated. In the stretching operation shown in FIG. 1, monofilament 16 is drawn through heating unit 30 by means of second godet station 31 which rotates at a higher speed than first godet station 21 to provide the desired stretch ratio. For larger size sutures, e.g., sizes 2 to 3/0, heating unit 30 may comprise a hot liquid bath (such as glycerol or water), through which monofilament 16 passes. For smaller size sutures, e.g., sizes 4/0 to 8/0, heating unit 30 may comprise a hot air convection oven chamber.

Following the stretching operation, monofilament 16 optionally may be subjected to additional stretching operations or an on-line annealing (relaxation) operation as a result of which the monofilament may undergo shrinkage. In accordance with methods that are known and described in the prior art, on line annealing with or without relaxation when desired is accomplished by driving the monofilament station through a second heating unit by a third godet station. For relaxation, the third godet station rotates at a slower speed than the second godet station thus relieving tension on the filament.

EXAMPLE 1

Monofilaments of poly(p-dioxanone) (inherent viscosity of 1.73 dl/g measured at 30° C. and a concentration of 0.25 g/dl in HFIP) were prepared employing the device shown in FIG. 1. The monofilament was placed around the separation rollers such that the monofilament made twelve passages around the godets in the first godet station prior to passing into the heating unit. This provided a dwell time of approximately ten minutes. The spinning and stretching conditions were as follows:

| CONDITIONS OF MANUFACTURING POLY(P-DIOXANONE) MONOFILAMENT | |
|---|---|
| Process Conditions | |
| | Extrusion Operation |
| extruder screw, rpm | 1.2 |
| pump rpm | 10.2 |
| driven roller, mpm | 3.9 |
| barrel temp., °C., zone A | 95 |
| barrel temp., °C., zone B | 128 |
| barrel temp., °C., zone C | 129 |

| -continued | |
|---|---|
| CONDITIONS OF MANUFACTURING POLY(P-DIOXANONE) MONOFILAMENT | |
| Process Conditions | |
| clamp temp., °C. | 129 |
| adapter temp., °C. | 130 |
| pump temp., °C. | 132 |
| barrel melt temp., °C. | 128 |
| pump melt temp., °C. | 127 |
| spinneret melt temp., °C. | 127 |
| barrel pressure, psi | 1450 |
| pump pressure, psi | 500 |
| pump size, cc per revolution | 0.16 |
| diameter of spinneret orifices, mm | 1.25 |
| no. of spinneret orifices | 1 |
| quench bath temp., °C. | 21 |
| depth of driven roller, cm | 16.5 |
| | Stretching (Orienting) Operation |
| first stretching, air oven temp., °C. | 50 |
| first godet station, mpm | 4 |
| second godet station, mpm | 20 |
| second stretching, liquid bath (Glycerol) temp., °C. | 95 |
| third godet station, mpm | 26 |
| draw ratio | 6.5:1 |

For comparison purposes, a control monofilament was prepared using the same extrusion and stretching conditions, however, the control monofilament made only a single pass through the first godet station before entering the heating unit in accordance with conventional monofilament preparation techniques.

The physical properties of the monofilament of Example 1 prepared in accordance with the present invention and the control monofilament were determined by an Instron Tensile Tester using the following procedures:

| PROCEDURES FOR MEASURING PHYSICAL PROPERTIES OF POLYETHERIMIDE ESTER MONOFILAMENT SUTURES | |
|---|---|
| Physical Property | Test Procedure |
| knot-pull strength, kpsi | U.S. Pat. No. XXI, tensile strength, sutures (881) |
| straight-pull strength, kpsi | ASTM D2256-88 |
| elongation at break, % | ASTM D2256-88 |

The results of these tests are set forth in the following Table I:

TABLE I

| | Straight-Pull Strength | Knot-Pull Strength | Elongation at Break |
|---|---|---|---|
| EXAMPLE I | 94 kpsi | 45 kpsi | 28% |
| CONTROL | 27 kpsi | 11 kpsi | 20% |

As can be seen by the data in Table I, the monofilament which was allowed for dwell for 10 minutes after quenching exhibited superior physical characteristics.

Obviously, modifications and variations of the present invention are possible in light of the above teachings. It is therefore to be understood that changes may be made in particular embodiments of the invention described which are

What is claimed is:

1. A monofilament suture manufacturing process comprising the steps of melt extruding and quenching a polymer to provide a solidified monofilament; subjecting the monofilament to one or more subsequent operations selected from the group consisting of drawing, stretching, heating and annealing; and exposing the monofilament to ambient conditions for a predetermined period of time of about 2 minutes to about 30 minutes prior to subjecting the monofilament to the subsequent operation.

2. The method of claim 1 wherein the monofilament is exposed to ambient conditions for a period of time ranging from about 5 minutes to about 20 minutes.

3. The method of claim 1 wherein the polymer comprises a bioabsorbable polymer.

4. The method of claim 3 wherein the bioabsorbable polymer comprises a homopolymer, copolymer or blend obtained from one or more monomers selected from the group consisting of glycolide, glycolic acid, lactide, lactic acid, p-dioxanone, epsilon-caprolactone and trimethylene carbonate.

5. The method of claim 4 wherein the bioabsorbable polymer comprises a blend of homopolymers or copolymers obtained from one or more monomers selected from the group consisting of glycolide, glycolic acid, lactide, lactic acid, p-dioxanone, epsilon-caprolactone and trimethylene carbonate.

6. The method of claim 1 wherein the thermoplastic polymer comprises a nonbioabsorbable polymer.

7. The method of claim 6 wherein the nonbioabsorbable polymer is polyethylene, polypropylene, nylon, polyethylene terephthalate, polybutylene terephthalate and polyvinylidene fluoride.

* * * * *